United States Patent [19]
Anderson

[11] Patent Number: 5,092,669
[45] Date of Patent: Mar. 3, 1992

[54] OPTICAL DEVICE AND METHOD FOR USING SAME

[75] Inventor: Duncan J. Anderson, London, United Kingdom

[73] Assignee: Migra Limited, United Kingdom

[21] Appl. No.: 494,575

[22] Filed: Mar. 16, 1990

[51] Int. Cl.$^5$ .............................................. A61B 3/00
[52] U.S. Cl. ..................................... 351/203; 351/158
[58] Field of Search ................ 351/203, 206, 221, 158

[56] References Cited

U.S. PATENT DOCUMENTS

| | | | |
|---|---|---|---|
| 3,612,651 | 10/1971 | McCurdy | 351/158 |
| 4,396,259 | 8/1983 | Miller | 351/158 |
| 4,938,582 | 7/1990 | Leslie | 351/158 |

FOREIGN PATENT DOCUMENTS

| | | |
|---|---|---|
| 1044833 | 10/1966 | United Kingdom . |
| 2064812 | 6/1981 | United Kingdom . |
| 2196442 | 4/1988 | United Kingdom . |

OTHER PUBLICATIONS

"The Treatment of Migraine with Variable Frequency Photo-Stimulation," D. J. Anderson, *Headache* 29:154-155, 1989.

"Light Relief for Mighty Migraines," *The Daily Telegraph*, Jan. 9, 1990.

*Primary Examiner*—Paul M. Dzierzynski
*Attorney, Agent, or Firm*—Lerner, David, Littenberg, Krumholz & Mentlik

[57] ABSTRACT

Apparatus is disclosed for directing flashes of light into the eyes of a user. LED's 17 are mounted in the eyepieces of goggles 3 or spectacles 43 to face the eyes of a wearer. The goggles 3 or spectacles 43 are opaque and are provided with opaque flanges 9 to avoid ambient light reaching the eyes of a wearer. The frequency and brightness of the flashes is variable. The device is useful in the treatment of migraine, pre-menstrual syndrome, insomnia and nervous tension. Alternatives are disclosed using remote light sources 51 and optic fibres 53 or mirrors 57, mechanical or electro-optic shutters 59, 61, and arrangements using a common light source 51 for both eyes.

28 Claims, 4 Drawing Sheets

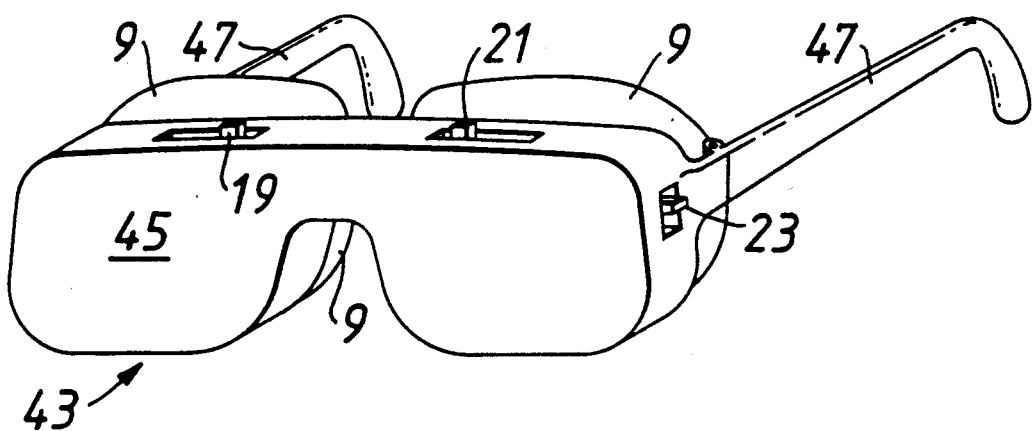
FIG. 4.
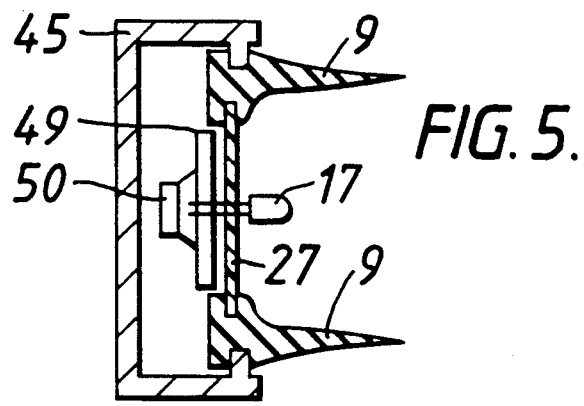
FIG. 5.
FIG. 6.
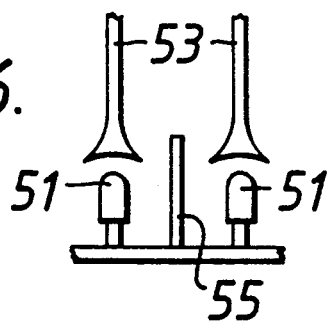
FIG. 7.

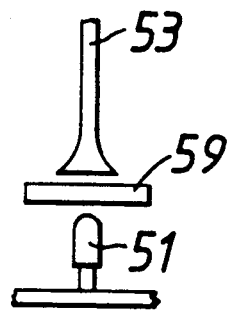
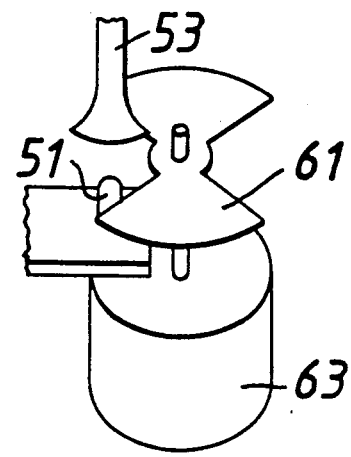
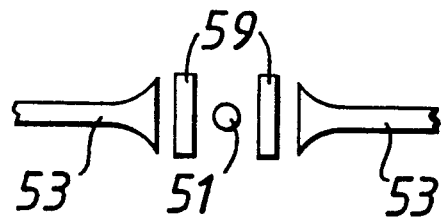
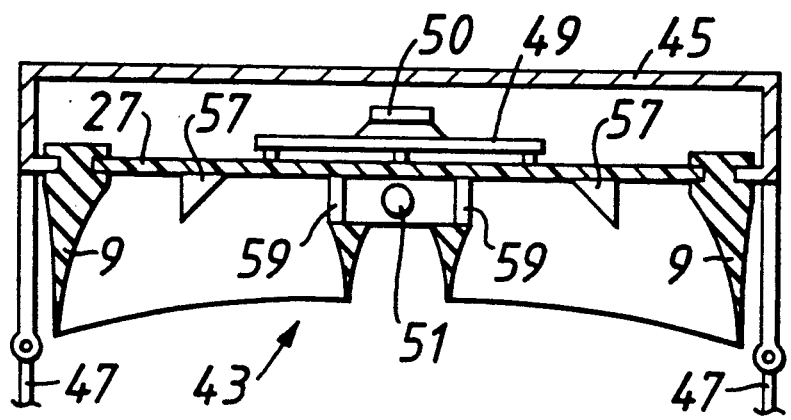

OPTICAL DEVICE AND METHOD FOR USING SAME

BACKGROUND OF THE INVENTION

The present invention relates to apparatus for delivering flashes of light to the eyes, and to methods of using the apparatus. The invention has particular, but not exclusive, application to the treatment and prevention of migraine, pre-menstrual syndrome, insomnia and nervous tension. Attention is directed to the applicant's publication "The Treatment of Migraine with Variable Frequency Photo-Stimulation" D. J. Anderson, Headache, Mar. 1989, pages 154 and 155, which is incorporated herein by reference.

The following definition of migraine has been given in J. N. Blau "Towards a Definition of Migraine Headache", Lancet, 1984, 1, pages 444 to 445. "Episodic headache lasting from 2 to 72 hours with total freedom between attacks. The headaches must be associated with visual or gastrointestinal disturbance or both. The visual symptoms occur as an aura before and/or photophobia during the headache phase. If there are no visual but alimentary disturbances, then vomiting must feature in some attacks." An alternative definition is given in "Classification of headache disorders, cranial neuralgias and facial pain; and diagnostic criteria for primary headaches disorders" available from the International Headache Society and abbreviated from Cephalalgia 1988; 8 suppl. 7:1–69, which is incorporated herein by reference.

Pre-menstrual syndrome has been defined as "the cyclic occurrence of symptoms that are of sufficient severity to interfere with some aspects of life and which appear with consistent and predictable relationship to menses" in Endicott J., Halbreich U., Schacht S. and Nee J. "Premenstrual changes and affective disorders" Journal of Psychosomatic Medicine 1981, Vol. 43, page 519, and quoted in "The Premenstrual Syndromes" ed. L. H. Gise, published 1988 by Churchill Livingstone, New York, Edinburgh, London, Melbourne.

Insomnia has been defined as consisting of "difficulty in initiating or maintaining sleep at least three times a week for at least a month. The loss of sleep produces significant day time fatigue or impaired occupational or social functioning. In typical cases, sleep latency exceeds 30 minutes or sleep efficiency is less than 85%", in "Phychiatric Dictionary" 6th edition, ed. R. J. Campbell 1989, Oxford University Press. Further details may be found in "Diagnostic and Statistical Manual of Mental Disorders" 3rd edition, Revised 1987, which is often referred to as "DSM-111-R". Further information is also available in "Oxford Textbook of Psychiatry", ed. Michael Gelder, 1989, Oxford University Press, especially at pages 399 and 400.

Nervous tension or stress is a psychological state with physiological consequences including increased muscle tension and an inability to relax, and is often accompanied by difficulty in concentrating and difficulty in sleeping.

All of these conditions are distressing or unpleasant for their sufferers. Although some advances have been made in understanding the causes of these conditions, there remains a need for curative and/or preventative treatments which are cheap, simple and effective.

It has been suggested by G. D. Solomon "Slow wave photic stimulation in the treatment of headache—a preliminary study", Headache 1985, 25, pages 444 to 446, that the use of light at a frequency range of 1 to 3 Hz for 5 minutes provided relief for muscle contraction headaches but not for migraine. The enhancement of brain alphawaves by bio-feedback has been used in the treatment of people with migraine, and according to M. J. Cohen, D. L. McCarthar and W. H. Rickles "Comparison of four bio-feedback treatments for migraine headaches: physiological and headache variables", Psychosomatic Medicine, 1980, 42, pages 463 to 480, this reduced the number of migraine headaches per week but did not change intensity, duration or disability of the headaches. It has been suggested, by D. Lewis "The alpha plan", published by Methuen in London in 1986, at page 26, that red stroboscopic light tends to produce rapid and powerful alpha brain rhythms in the occipital cortex. These prior art publications do not lead to any clear or definite conclusion about either the causes or the treatment of migraine, and at present treatments are typically based on the control of diet and the use of drugs.

Pre-menstrual syndrome is generally considered to be caused by hormonal changes during the menstrual cycle, and is generally treated using drugs.

Insomnia and nervous tension or stress are generally treated psychologically or with drugs, especially the major and minor tranquilisers.

British Patent 2,196,442, of the present applicant, proposes a device for flashing light into the eyes of a user, either alternately or synchronously. It is suggested that the light should be provided by light sources mounted in the eyepieces of goggles. No disclosure is given of the frequency of the flashes. There is no suggestion that the goggles should be in any way darkened or obscured so as to reduce the ambient light also reaching the eyes of a user. There is no suggestion of any purpose or beneficial effect of use of the device.

SUMMARY OF THE INVENTION

It is an object of the present invention to provide a method of treating migraine, pre-menstrual syndrome, insomnia and/or nervous tension by flashing light into the eyes of a patient.

It is a further object of the present invention to provide a method as aforesaid in which substantially all ambient light is prevented from reaching the eyes of the patient.

It is a further object to provide a method as aforesaid in which light is flashed into the patient's eyes through closed eyelids.

It is a further object of the present invention to provide apparatus for flashing light into the eyes of a user while preventing entry of substantially all ambient light.

It is a further object of the present invention to provide the flashes of light to the eyes of the user alternately. Alternatively, it is an object of the present invention to provide the flashes of light to the eyes of a user synchronously.

According to one aspect of the present invention there is provided a method of treating migraine, pre-menstrual syndrome, insomnia or nervous tension, either in advance or during experience of the symptoms by a sufferer, in order to reduce, remove or prevent symptoms, by flashing light into the eyes of the sufferer. The method may comprise placing over the eyes of a patient eyepiece means adapted to prevent substantially all light reaching the eyes of the patient, and flashing light into the eyes of the patient while the eyepiece means remains over the eyes of the patient. Preferably, the light is flashed into the patient's eyes through closed eyelids. The flashes in the respective eyes may be either in phase or out of phase, but it is currently believed that the most beneficial effect is achieved if the flashes of light to the respective eyes are substantially alternate.

The frequency and brightness of the light are both preferably variable, and both preferably under the control of the patient. Preferably, the frequency range covers at least 0.5 to 50 Hz. However, the lower limit of the frequency range may be greater, for example 1 Hz or even 5 Hz, and of course it may be lower, e.g. right down 0 Hz (continuous). The upper limit of the frequency range is preferably at least 100 Hz, and may be at least 200 Hz. The flashes of light preferably have an intensity at 2 cm from the eyelids of at least the range 10 to 500 millicandela. Brighter flashes might be provided, e.g. up to 1000 millicandela. Very bright flashes may be unpleasant, or even damage the retina, and the maximum brightness available preferably prevents this. For this reason, it is presently preferred that the maximum brightness is less than 2000 millicandela.

The present invention also provides apparatus for delivering flashes of light to the eyes in which substantially all ambient light is excluded. In an embodiment of the present invention, there is provided apparatus for delivering flashes of light to the eyes, comprising eyepiece means adapted to be placed over the eyes of a user in use and prevent entry of substantially all ambient light into the eyes of the user, light source means adapted to deliver light to the eyes of a user having eyepiece means placed over his or her eyes, and control means adapted to energise the light source means, the light source means emitting light when energised by the control means.

The control means may be operable to energise a light source means intermittently, so as to cause the light source means to emit light in flashes. Alternatively, light interrupting means may be provided, operable to divide continuously emitted light from the light source means into flashes. Various devices may be provided as the light interrupting means, such as a rotating slotted disc, or an optoelectric device such as a liquid crystal shutter.

A light source of a light source means may be mounted on the eyepiece means facing the eyes of the user. In an alternative embodiment, deflection means such as mirrors and/or optical fibre means are provided to convey light from the light source means to the eyes of the user.

The invention will now be described in more detail with reference to the accompanying drawings, which illustrate embodiments of the present invention provided by way of non-limiting example.

BRIEF DESCRIPTION OF THE DRAWINGS

In the drawings:

FIG. 4 illustrates schematically a second embodiment of the present invention;

FIG. 5 is a schematic section through an eyepiece of the spectacles of FIG. 4;

FIG. 6 shows an alternative construction with remote light sources and optical fibre means;

FIG. 7 shows an alternative construction with a remote light source and a mirror;

FIG. 8 shows an alternative construction with a liquid crystal shutter;

FIG. 9 shows an alternative construction with a mechanical shutter;

FIG. 10 shows an alternative construction with a single light source for both eyes and optical fibre means; and FIG. 11 shows an alternative construction with a single light source for both eyes and mirrors.

DESCRIPTION OF PREFERRED EMBODIMENTS

Figure 1:
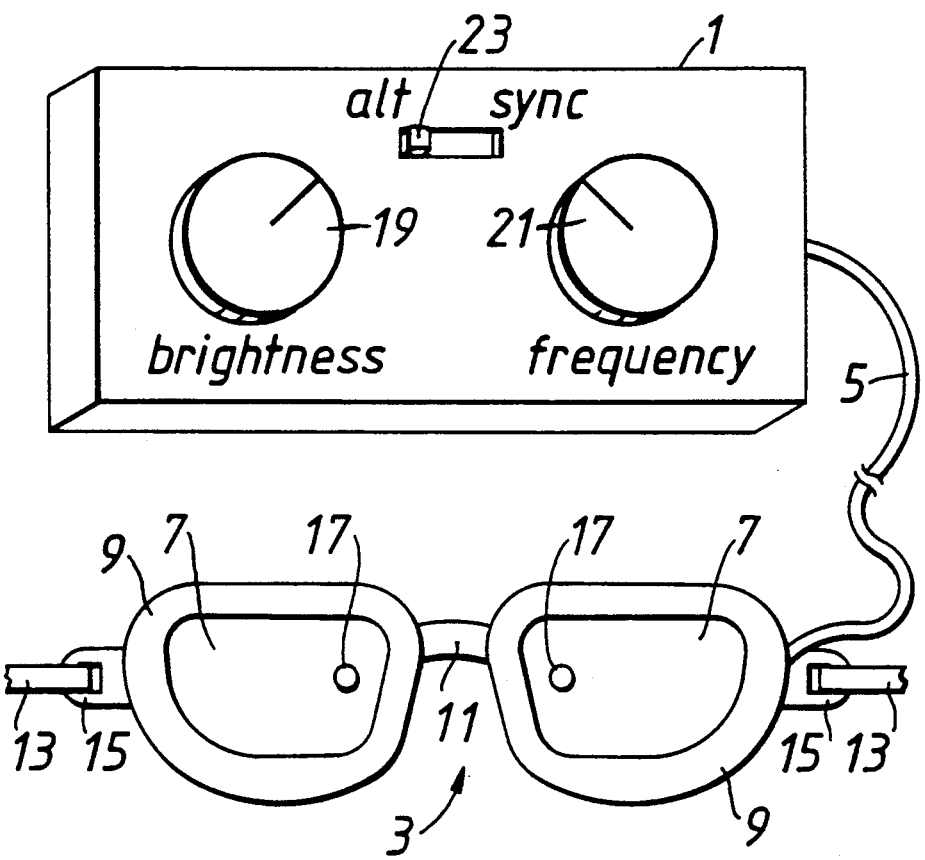
FIG. 1 illustrates schematically a first embodiment of the present invention.

FIG. 1 shows a first embodiment of the present invention. This embodiment comprises a control box 1 and a pair of goggles 3, connected by a signal line 5.

The goggles 3 resemble conventional swimmers' goggles having separate eyepieces. Each eyepiece comprises a plate 7, surrounded by an elastomeric flange 9. The eyepieces are connected by a flexible bridge 11, and a strap 13 extends around the head of a user, so as to hold the goggles 3 over the eyes, from eyelet fittings 15 on the sides of the eyepieces remote from the bridge 11.

Unlike conventional swimmers' goggles, the plates 7 are opaque, and each carries a light source, conveniently a light emitting diode (LED) 17 on the side towards the user's eyes in use. The flanges 9 extend from the plates 7 towards the face of a wearer, and may make contact with the face, and are opaque so as to substantially prevent any light from reaching the eyes of a wearer around the sides of the plates 7. Thus, when the goggles 3 are being worn, substantially the only light which can reach the eyes of the wearer comes from the LED's 17.

The LED's 17 are powered by electrical signals carried in wires in the signal line 5. As shown in FIG. 1, the signal line 5 is connected to the goggles 3 at the eyelet fitting 15 side of one eyepiece. The signals are carried within the plate 7 to the LED 17, and also through the bridge 11 to the LED 17 of the other plate 7.

Other arrangements are possible. The signals could be carried from one plate 7 to the other by wires separate from the bridge 11. Separate signal-carrying wires could be provided to each plate 7. The wires could be connected directly to the LEDs 17, rather than having the signals carried within the plates 7.

The signals to drive the LED's 17 are provided to the signal line 5 by the control box 1. The control box 1 has a brightness control 19, in the form of a rotatable knob, which also acts as an on/off switch. This controls the brightness of the light emitted by the LED's. The driving signals to the LED's 17 are provided intermittently, so as to make the LED's 17 flash, and the frequency of these flashes is controlled by a frequency control 21, also in the form of a rotatable knob. Additionally, a switch 23 selects between the two possibilities of the two LED'S 17 flashing synchronously or flashing alternately.

The brightness control 19 permits variation of the brightness of the LED's 17, preferably substantially continuously but alternatively in steps, from zero (i.e. off) to a light emission by each LED 17 of preferably at least 500 millicandela. A greater maximum brightness, e.g. at least 1000 millicandela, may be provided. The lowest frequency selectable using the frequency control 21 is preferably 0.5 Hz or less, and may be 0 Hz (continuous), although higher minimum frequencies are possible e.g. 2 Hz or even 5 Hz. The maximum frequency is preferably at least 50 Hz, more preferably at least 100 Hz, and most preferably at least 200 Hz.

Figure 2:
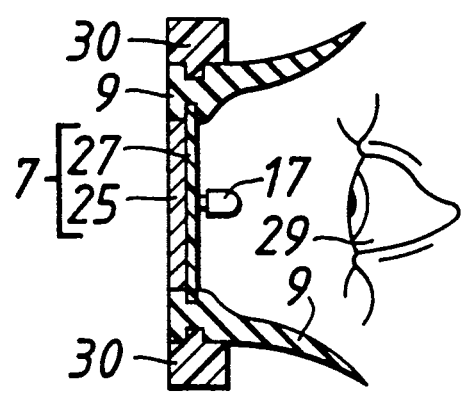
FIG. 2 is a schematic section through an eyepiece of the goggles of FIG. 1.

The construction of the goggles 3 is shown in more detail in FIG. 2, which is a vertical section through one of the plates 7 and its associated flange 9. The plate 7 comprises an opaque covering 25, on its side away from the LED 17, and a reflective layer 27 on its side towards the LED 17. The reflective layer 27 tends to increase the amount of light from the LED 17 reaching the eye 29 of a wearer. The wires to power the LED 17 pass from the signal line 5 to the LED 17 between the reflective layer 27 and the opaque covering 25. A plastic frame 30, hidden in FIG. 1 behind the flange 9, extends around the flange 9 at the level of the plate 7, to hold the construction together.

In an alternative construction, the reflective layer 27 is replaced by a circuit board on which the LED 17 is mounted, e.g. by surface mounting. Solder on the surface of the circuit board reflects light from the LED 17, and the circuit board assists the opaque covering 25 to block ambient light.

In use, a user places the goggles 3 over his or her eyes, adjusts them so as to exclude substantially all ambient light, and tightens strap 13 to hold the goggles 3 in place. The brightness control 19 is then rotated to turn on the LED's 17, and to adjust the brightness thereof. The frequency of the flashing of the LED's is adjusted using the frequency control 21, and the switch 23 is operated to select either synchronous flashing or flashes alternating between the two eyes. Preferably, the user closes his or her eyes, so that the eyelid acts to diffuse the light from the LED's 17. The brightness and frequency of the flashes are adjusted by the user to whatever values within the available ranges are desired.

The effectiveness of a device similar to that shown in FIGS. 1 and 2 for the treatment of migraine was tested on 7 patients. During the test period, a total of 50 migraines were recorded, and in 49 of these the patient regarded the migraine as being "helped" by use of the goggles. 36 of the migraines were rated as being "stopped" by use of the goggles. Patients were instructed to use the goggles at the onset of symptoms of a migraine, and the duration of each use was controlled by the patient. The durations of use ranged from 5 to 60 minutes, with a median of 30 minutes. The reported range of duration of headaches using the goggles was 5 minutes to 6 hours, with a median of 35 minutes, as compared with a range of 4 to 48 hours and a median of 6 hours without treatment. The devices used in this test had a maximum frequency of flashing of 50 Hz, and a maximum light output from the LED's of 500 millicandela. Most patients used the goggles at the brightest setting and near the top of the frequency range. For this reason, it is preferred that the maximum brightness of the light sources is greater than 500 millicandela, e.g. at least 1000 millicandela. Similarly, it is preferred that the maximum frequency of flashing is above 50 Hz. Further details of this trial are given in the above-mentioned publication in Headache by the present applicant.

Follow-up studies and informal tests indicate that use of the apparatus tended to reduce the frequency with which migraines occurred, and suggested that benefits were obtained if the devices were used during a migraine and also if the devices were used during periods between migraines when no symptoms were present.

Additionally, there have been reports of a calming effect of using the device, and users feeling less tense and stressed, of users experiencing relief from sleeping difficulties, and also relief from pre-menstrual tension.

The mechanism by which the use of such a device assists users is not known. However, there have been reports that the bright flashes from the device embodying the present invention "cut through" the visual disturbances experienced as pre-migraine symptoms by many sufferers, and it is speculated that maybe the regular visual stimulation overrides other visual area brain activity and also tends to enforce a regular brain alpha rhythm, which may lead to the observed beneficial effects. However, this speculation has not been confirmed.

Figure 3:
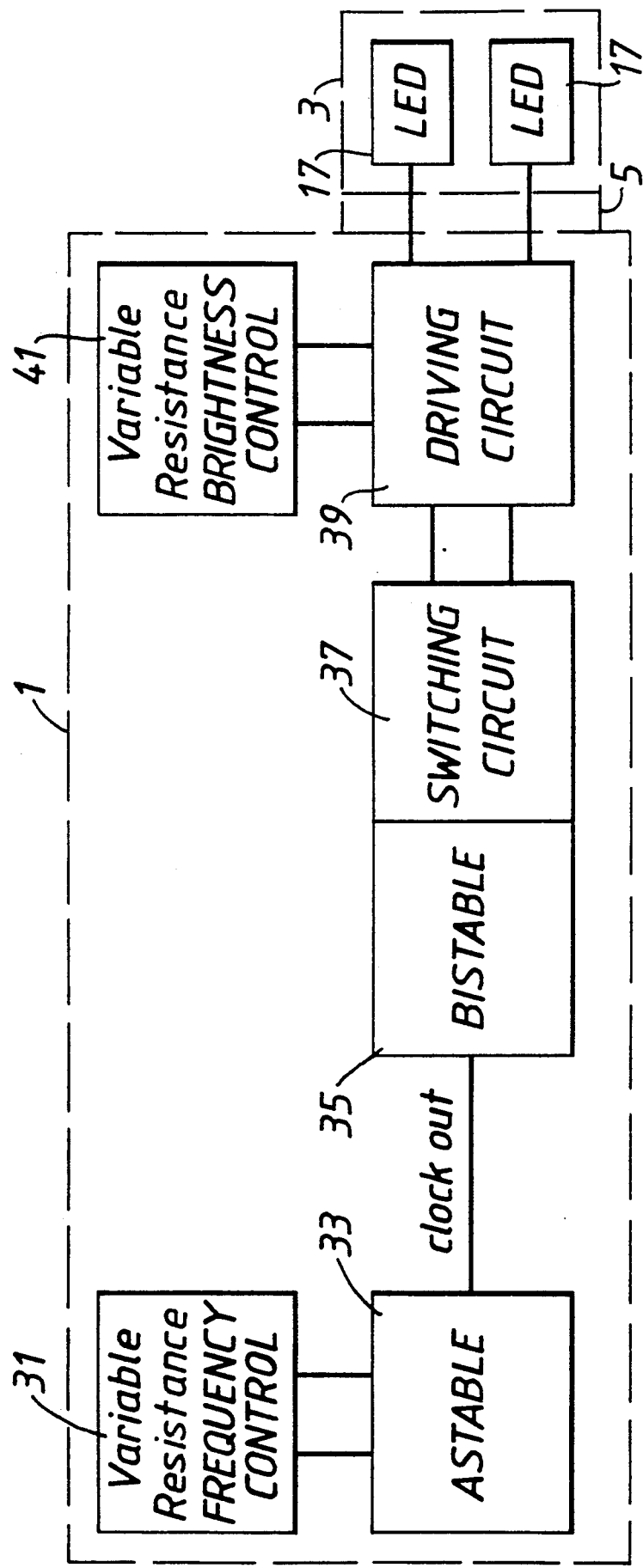
FIG. 3 is a block diagram of a control circuit for the embodiment of FIG. 1.

FIG. 3 illustrates in block form a circuit for controlling the embodiment of FIGS. 1 and 2. Rotation of the frequency control knob 21 varies the resistance of a variable resistor 31. The resistance of resistor 31 controls the output frequency of an astable circuit 33. Such circuit arrangements are well known, and may conveniently be based on the NE555 type of integrated circuit chip. The frequency range selected for the astable circuit 33 will be chosen in accordance with the frequency range for the flashes of the LED's 17.

The astable circuit 33 provides a squarewave clock output signal to a bistable 35, which halves its frequency. The output of the bistable 35 passes through a switching circuit 37 and is provided on two lines to a driving circuit 39. The switching circuit 37 is controlled by the switch 23. When synchronous flashing of the LED's 17 is selected, identical squarewave outputs from the bistable 35 are placed on the two lines from the switching circuit 37 to the driving circuit 39. When alternate flashing of the LED's 17 is selected, the signal on one of the lines from the switching circuit 37 to the driving circuit 39 is inverted, so that one signal is high when the other is low and vice versa The driving circuit 39 amplifies the signals received from the switching circuit 37, and provides the respective amplified signals via the signal line 5 to the LED's 17. The brightness of the flashes of light provided by the LED's 17 will depend on the amplitude of the drive signals provided by the driving circuit 39, and this is controlled by the resistance of a variable resistor 41. The resistance of variable resistor 41 is varied by rotation of the brightness control knob 19.

Preferably, the circuit of FIG. 3 is powered by an electric cell or battery provided in the control box 1, although means may be provided for powering the circuit from the mains. Rotation of the brightness control knob 19 also operates an on/off switch, not shown in FIG. 3, which preferably makes and breaks a connection between the power supply (battery) and the remainder of the circuit. As an alternative, a separate control may be provided for the on/off switch.

As will be appreciated by those skilled in the art, many alternatives to the circuit of FIG. 3 are possible. For example, the variable frequency clock signal may be provided by a voltage controlled oscillator, optionally followed by voltage dividing and/or multiplying circuits, and optionally forming part of a phase-locked loop. In this case, the frequency control 21 would directly or indirectly vary the control voltage applied to the voltage controlled oscillator. If desired, the entire circuit except for the devices a parameter of which is varied by the brightness and frequency controls 19,21, and possibly with the exception of high power output driving transistors, may be provided in a customised single integrated circuit.

FIG. 4 shows a second embodiment of the present invention. This embodiment is based on a construction similar to conventional spectacles rather than swimming goggles. Additionally, in the embodiment of FIG. 4 there is no control box 1, and the control circuit together with a battery is provided in the spectacles 43. FIG. 5 is a vertical section through one eyepiece of the spectacles 43.

In the second embodiment, an opaque cover 45 includes conventional spectacle arms 47 to fit behind a user's ears, and extends as a single piece across the front of the spectacles. This cover 45 holds in place the elastomeric flanges 9, as can be seen in FIG. 5, and thereby acts to hold the spectacles 43 together.

The LED's 17 are mounted facing the eyes of a person wearing the spectacles 43, in front of a reflective layer 27. The power leads for the LED's 17 extend through the reflective layer 27 to a printed circuit board 49, which also bears one or more circuit components, such as integrated circuit chips 50, forming the control circuit. The printed circuit board 49 is opaque, and assists in preventing ambient light from reaching the wearer's eyes through the spectacles 43.

As can be seen in FIG. 4, the brightness control 19 and frequency control 21 are provided as slider knobs in the top surface of the cover 45, and the synchronous/alternate switch 23 is provided at one side. Other convenient positionings are possible. As in the embodiment of FIG. 1, the brightness control 19 can also act as an on/off switch. Alternatively a separate on/off switch can be provided, e.g. at a position corresponding to the position of the synchronous/alternate switch 23 but on the other side of the spectacles 43. The spectacles of FIGS. 4 and 5 are operated and used in a manner corresponding to the use and operation of the goggles 3 in control box 1 of FIGS. 1 and 2.

As will be appreciated by those skilled in the art, various other arrangements are possible. In particular, the LED's 17 may be mounted on a spectacle-type device, similar to that shown in FIG. 4, but a separate control box 1 connected to the spectacle-type device by a signal line 5, as shown in FIG. 1, may be used.

FIGS. 6 to 11 show various possible alternatives in the construction of devices embodying the present invention.

In FIGS. 1 to 5, the light sources for the flashes of light directed to the user's eyes are light emitting diodes placed in front of the eyes so that light is provided directly to the eyes. Light sources other than light emitting diodes can be used. Additionally, the light sources may be positioned other than directly in front of the user's eyes, and deflection means may be provided to direct light from a light source to the eye. FIG. 6 shows first and second light sources 51, for the respective eyes, positioned side-by-side remote from the eyes. For example, they may be positioned on a circuit board in the control box 1. Each light source 51 is associated with a respective optical fibre 53, which carries the light from the light source 51 to the respective eye of the user. Where the light sources 51 are provided in a separate control box 1, the optical fibres 53 may be carried by the signal lne 5, which would then carry optical rather than electrical signals. In FIG. 6, a wall 55 is provided between the light sources 51 to ensure that each optical fibre 53 receives light only from its associated light source.

FIG. 7 is a view similar to FIG. 2, showing another alternative construction using light deflection means. In this construction, each light source 51 is provided at the top of each eyepiece of the goggles 3, so as to shine downwardly across the eyepiece. A mirror 57 mounted on the reflective layer 27 reflects light from the light source 51 into the eye 29 of the user.

In the preceding description, the flashes of light delivered to the eyes of a user have been created by flashing the sources of light. As an alternative, a continuous light source may be used together with light interrupting means. FIG. 8 shows an arrangement in which light from a light source 51 reaches an optical fibre 53 via an electro-optic device 59, such as a liquid crystal shutter, which can be controlled electrically to transmit or block light from the light source 51 to the optical fibre 53.

Other types of light interrupting means may be used. FIG. 9 shows a slotted disc 61, driven in rotation by a motor 63, which passes between a light source 51 and an optical fibre 53 so as to interrupt the light from the light source 51.

As will be appreciated by those skilled in the art, in the arrangements of FIGS. 8 and 9 the variable frequency signal, the frequency of which is controlled by the user via frequency control 21, controls the frequency of operation of the light interrupting means, rather than controlling the signal to the light source 51. I.e. it controls the frequency of operation of the electro-optic device 59 or the frequency of rotation of the slotted disc 61.

In the foregoing discussion, a separate LED 17 or light source 51 has been provided for each eye. However, arrangements are possible in which a common light source provides light for both eyes. Thus, in FIG. 10 a single light source 51 is provided, which emits light towards both of two optical fibres 53 to carry light to the eyes. In order to enable flashes of light to be directed to the two eyes alternately, the light source 51 is illuminated continuously, and respective independently controllable electro-optic shutters 59 are provided between the light source 51 and the respective optical fibres 53.

FIG. 11 shows a horizontal section through a modification of the embodiment of FIGS. 4 and 5. In this arrangement, a single light source 51 is provided in the bridge of the spectacles 43, directing light towards respective mirrors 57, which reflect the light into the respective eyes of a wearer. The light source 51 is illuminated continuously, and respective electro-optic shutters 59 are provided between the light source 51 and the respective mirrors 57.

Additionally, in the foregoing embodiments, the light source means has included no more than one light source per eye. However, multiple light source arrangements, of two or more light sources, may be used.

The foregoing embodiments and alternatives have been provided for illustration only, and are not to be construed as limiting the present invention. In particular, the present invention includes all modifications and alternatives falling within the scope of the accompanying claims.

What is claimed is:

1. An apparatus for delivering flashes of light to the eyes, comprising: eyepiece means adapted to be placed over the eyes of a user in use and prevent entry of substantially all ambient light into the eyes of the user, light source means adapted to deliver light to the eyes of a user having the eyepiece means placed over said eyes, flash control means adjustable to vary at least one of either the brightness of said flashes of light of the frequency of said flashes of light and operable in a mode of operation such that when in said mode of operation the flash control means causes light from the light source means to be delivered to the types of said user in flashes having a regular frequency at a set brightness.

2. An apparatus for delivering flashes of light to the eyes, comprising: eyepiece means adapted to be placed over the eyes of a user in use and prevent entry of substantially all ambient light into the eyes of the user, light source means adapted to deliver light to the eyes of a user having the eyepiece means placed over said eyes, and control means adapted to energize said light source means, the light source means emitting light having a set brightness when energized by the control means, the control means being operable in a mode of operation such that when in said mode of operation the control means automatically energizes the light source means intermittently so as to cause the light source means to emit light in flashes having a regular frequency at a set brightness and said control means being adjustable to vary at least one of either said regular frequency or said set brightness.

3. An apparatus for delivering flashes of light to the eyes, comprising: eyepiece means adapted to be placed over the eyes of a user in use and prevent entry of substantially all ambient light into the eyes of the user, light source means adapted to deliver light to the eyes of a user having the eyepiece means placed over said eyes, and control means adapted to energize said light source means, the light source means emitting light having a set brightness when energized by the control means, and further comprising light interrupting means operable to divide continuously emitted light from said light source means into flashes and at least one of either the control means or the light interrupting means is adjustable, to vary the brightness of said flashes of light or the frequency of said flashes of light respectively, such that the resulting flashes of light have a regular frequency at a set brightness.

4. The apparatus according to claim 2 wherein said light source means comprises at least one light source mounted on the eyepiece means facing the eyes of a user having the eyepiece means placed over his or her eyes, to emit light directly to the eyes of the user.

5. The apparatus according to claim 4 wherein said light source means comprises first and second said light sources, mounted facing the left and right eyes of the user respectively.

6. The apparatus according to claim 2 further comprising light deflection means provided to convey light from said light source means to the eyes of the user.

7. The apparatus according to claim 6 wherein said light deflection means comprises optical fibre means.

8. The apparatus according to claim 7 wherein said optical fibre means has a first end adapted to receive light from the light source means and a second end mounted on the eyepiece means facing the eyes of a user having the eyepiece means placed over his or her eyes.

9. The apparatus according to claim 6 in which the said light deflection means comprises at least one mirror.

10. The apparatus according to claim 2 wherein the flash control means comprises frequency control means, adjustable to vary the frequency of said flashes of light.

11. The apparatus according to claim 10 wherein the frequency control means is adjustable to vary the frequency of said flashes of light over a range of at least from 5 Hz to 50 Hz.

12. The apparatus according to claim 2 wherein the control means comprises brightness control means, adjustable to vary the brightness of said flashes of light.

13. The apparatus according to claim 3 wherein said light source means comprises at least one light source mounted on the eyepiece means facing the eyes of a user having the eyepiece means placed over said eyes, to emit light directly to the eyes of the user.

14. The apparatus according to claim 13 wherein said light source means comprises first and second said light sources, mounted facing the left and right eyes of the user respectively.

15. The apparatus according to claim 3 further comprising light deflection means provided to convey light from said light source means to the eyes of the user.

16. The apparatus according to claim 15 wherein said light deflection means comprises optical fiber means.

17. The apparatus according to claim 16 in which said optical fiber means has a first end adapted to receive light from the light source means and a second end mounted on the eyepiece means facing the eyes of a user having the eyepiece means placed over said eyes.

18. The apparatus according to claim 17 wherein said light deflection means comprises at least one mirror.

19. The apparatus according to claim 3 wherein said light interrupting means is operable to divide continuously emitted light from said light source means into flashes at a predetermined frequency of flashes.

20. The apparatus according to claim 19 wherein the control means comprises frequency control means adjustable to vary the frequency at which said light interrupting means divides said continuously emitted light and thereby to vary said frequency of flashes.

21. The apparatus according to claim 3 in which the frequency control means is adjustable to vary said frequency of flashes over a range of at least from 5 Hz to 50 Hz.

22. The apparatus for delivering flashes of light to the eyes, comprising: eyepiece means adapted to be placed over the eyes of a user in use and prevent entry of substantially all ambient light into the eyes of the user, light source means adapted to deliver light tot he eyes of a user having the eyepiece means placed over said eyes, means to set the brightness and frequency of said flashes such that the flashes of light have a regular and set frequency and a set brightness.

23. A method of treating a condition selected from the group consisting of migraine headache, pre-menstrual syndrome, insomnia or nervous tension comprising the steps of placing over the eyes of a patient eyepiece means adapted to prevent substantially all ambient light reaching the eyes of the patient, and flashing light of a set brightness and a regular frequency into the eyes of a patient in need of such treatment while the eyepiece means remains over the eyes of the patient.

24. The method according to claim 23, wherein the flashes of light into the respective eyes are in phase.

25. The method according to claim 23 wherein the flashes of light into the respective eyes are out of phase.

26. The method according to claim 23 wherein the step of flashing light is performed while the patient has a migrainous headache.

27. The method according to claim 23 wherein the step of flashing light is performed while the patient experiences pre-headache migrainous symptoms.

28. The method according to claim 23 wherein the light is flashed into the patients eyes through closed eyelids during said step of flashing light.

* * * * *

UNITED STATES PATENT AND TRADEMARK OFFICE
CERTIFICATE OF CORRECTION

PATENT NO. : 5,092,669
DATED     : March 3, 1992
INVENTOR(S) : Anderson

It is certified that error appears in the above-identified patent and that said Letters Patent is hereby corrected as shown below:

```
Column 7, line 37, "in" should read --and--.
Column 7, line 64, "lne" should read --line--.
Column 9, line 7, "types" should read --eyes--.
Column 10, line 39, the first occurrence of "The" should
                    read --An--.
Column 10, line 43, "tot he" should read --to the--.
```

Signed and Sealed this

First Day of June, 1993

Attest:

MICHAEL K. KIRK

Attesting Officer

Acting Commissioner of Patents and Trademarks